US012753390B2

(12) United States Patent
Ikebuchi et al.

(10) Patent No.: US 12,753,390 B2
(45) Date of Patent: Oct. 6, 2026

(54) METHOD FOR PRODUCING CELL SHEET

(71) Applicant: KANEKA CORPORATION, Osaka (JP)

(72) Inventors: Fumie Ikebuchi, Kobe (JP); Tomoyuki Nakaishi, Kobe (JP); Fumiko Hara, Kobe (JP)

(73) Assignee: KANEKA CORPORATION, Osaka (JP)

( * ) Notice: Subject to any disclaimer, the term of this patent is extended or adjusted under 35 U.S.C. 154(b) by 381 days.

(21) Appl. No.: 18/285,006

(22) PCT Filed: Mar. 29, 2022

(86) PCT No.: PCT/JP2022/015459

§ 371 (c)(1),
(2) Date: Sep. 29, 2023

(87) PCT Pub. No.: WO2022/210712

PCT Pub. Date: Oct. 6, 2022

(65) Prior Publication Data

US 2024/0182857 A1 Jun. 6, 2024

(30) Foreign Application Priority Data

Mar. 30, 2021 (JP) ................................ 2021-056660
Mar. 9, 2022 (JP) ................................ 2022-035917

(51) Int. Cl.
*C12N 5/077* (2010.01)
*C12M 1/00* (2006.01)

(52) U.S. Cl.
CPC ........... *C12N 5/0652* (2013.01); *C12M 23/20* (2013.01); *C12N 2500/38* (2013.01); *C12N 2501/999* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 2013/0101659 | A1 | 4/2013 | Sawa et al. |
| 2017/0216362 | A1 | 8/2017 | Oka et al. |
| 2020/0237520 | A1 | 7/2020 | Vaquette et al. |

FOREIGN PATENT DOCUMENTS

| | | | |
|---|---|---|---|
| JP | 2005-117939 | A | 5/2005 |
| JP | 2014-140384 | A | 8/2014 |
| JP | 2015-165921 | A | 9/2015 |
| JP | 2017-000626 | A | 1/2017 |
| JP | 2017-132744 | A | 8/2017 |
| JP | 2019-170380 | A | 10/2019 |
| JP | 2019-533429 | A | 11/2019 |
| JP | 2020-110179 | A | 7/2020 |
| JP | 2020-530375 | A | 10/2020 |
| JP | 2021-7340 | A | 1/2021 |
| WO | WO 2014/209856 | A1 | 12/2014 |
| WO | WO 2018/033596 | A1 | 2/2018 |
| WO | WO 2020/150308 | A1 | 7/2020 |
| WO | WO 2020/166279 | A1 | 8/2020 |
| WO | WO 2020/226043 | A1 | 11/2020 |

OTHER PUBLICATIONS

Choi et al. "Effect of Ascobic Acid on Bone Marrow-Derived Mesenchymal Stem Cell Proliferation and Differentiation" (2008), J Biosci & Bioengin, vol. 105, No. 6: 586-594. (Year: 2008).*
Shotorbani et al. "Cell sheet biofabrication by co-administration of mesenchymal stem cell secretome and vitamin C on thermoresponsive polymer", (2018), J Mater Sci, 29: 170, (Year: 2018).*
Abe, Tatsuya, "Development of multi-layered stem cell sheet transplant material for periodontal regenerative therapy", (Grant-in-Aid for Scientific Research (Grants-in-Aid for Scientific Research) Research Results Report. Japan Society for the Promotion of Science.), 2013, 8 pgs.
International Search Report (PCT/ISA/210) issued in PCT/JP2022/015459 dated May 24, 2022.
International Written Opinion (PCT/ISA/237) issued in PCT/JP2022/015459 dated May 24, 2022.
Kim et al., "Stable cell adhesion affects mesenchymal stem cell sheet fabrication: Effects of fetal bovine serum and human platelet lysate", Journal of Tissue Engineering and Regenerative Medicine, May 2020, 14 (5): 741-753.
Nakamura. K. et al., "ROCK inhibitor Y-27632 maintains the proliferation of confluent human mesenchymal stem cells", Journal of Periodontal Research. 2014. vol. 49. pp. 363-370.

* cited by examiner

*Primary Examiner* — Teresa E Knight
(74) *Attorney, Agent, or Firm* — Birch, Stewart, Kolasch & Birch, LLP

(57) ABSTRACT

A method for preparing a cell sheet having a durable strength in practical use with good reproducibility within a period of time as short as possible, regardless of a culture medium additive or a type of culture vessel to be used is provided. The method for producing a cell sheet comprises a step of culturing mesenchymal stem cells in a medium containing an ascorbic acid species at 0.3 mM or higher and a ROCK (Rho-associated coiled-coil forming kinase) inhibitor to prepare mesenchymal stem cells in a sheet-like form in a culture vessel, wherein the ascorbic acid species is a water-soluble ascorbic acid derivative or a mixture of a water-soluble ascorbic acid derivative and ascorbic acid.

9 Claims, 6 Drawing Sheets

(A) (B)

METHOD FOR PRODUCING CELL SHEET

TECHNICAL FIELD

The present invention relates to a method for producing a cell sheet consisting of mesenchymal stem cells.

BACKGROUND ART

For the purpose of reproduction or functional restoration of tissue damaged because of diseases or injuries, regenerative medicine using a cell such as a stem cell has been performed. In particular, a cell sheet, which can be applied directly to an affected area to perform treatment and administered topically, has drawn attention as a means of treatment with few side effects and development thereof toward the practical use has been in progress. For treatment of several diseases, such as ischemic heart disease, severe burns, and corneal epithelial stem cell exhaustion, a cell sheet is actually used.

A method for producing a cell sheet includes, for example, a method of preparing a cell itself in a sheet form, in addition to a method of proliferating or retaining a cell using a matrix such as a fibrous sheet as a scaffold. While a matrix that would not adversely affect in the body has been developed, a method of preparing a cell itself in a sheet form is expected and various studies have been made. In fact, however, methods for sheet preparation significantly vary depending on types of cells of interest, and generally reported methods for producing a cell sheet may not be adopted for preparation of a sheet of a particular type of cells, such as mesenchymal stem cells. In addition, preparing a cell sheet in good quality often requires labors and costs such as a long culture period.

A report of actually preparing a cell sheet of mesenchymal stem cells is that a cell sheet was obtained by culturing mesenchymal stem cells in a medium containing ascorbic acid for 2 weeks or longer (Patent Literature: 1). As a method for preparing a cell sheet be applied to a scaffold construct and be differentiated afterwards, for example, culturing in a medium containing ascorbic acid has been reported (Patent Literatures 2 and 3).

Components to be added to a medium are considered to affect cell sheet formation. For example, a human platelet lysate is known as an additive that promotes mesenchymal stem cell proliferation, but it is impossible to obtain a cell sheet in a medium containing a human platelet lysate (Non-Patent Literature 1).

CITATION LIST

Patent Literature [0006]

Patent Literature 1: JP 2005-117939 A
Patent Literature 2: JP 2017-000626 A
Patent Literature 3: JP 2020-530375 A

Non-Patent Literature

Non-Patent Literature 1: Journal of Tissue Engineering and Regenerative Medicine, May 2020, 14 (5): 741-753

SUMMARY OF INVENTION

Technical Problem

The present inventors had attempted to prepare a cell sheet of mesenchymal stem cells by the reported methods indicated above and found that a culture period longer than the reported period is necessary to obtain a cell sheet having a durable strength in practical use. In order to promote cell proliferation, the present inventors used an additive, such as a human platelet lysate, and found that a sheet of good quality would not be formed. In addition, the present inventors used a culture vessel coated with a temperature-sensitive polymer to peel cultured cells without damaging the cells, which has been often used for cell sheet preparation, and found that such culture vessel may adversely affect cell sheet formation.

Based on the problem above, an object of the present invention is to provide a method for preparing a cell sheet having a durable strength in practical use with good reproducibility within a period as short as possible, regardless of a culture medium additive or a type of culture vessel to be used.

Solution to Problem

As a result of an intensive studies to achieve the above object, the present inventors found that a sheet of good quality would be prepared within a short period using ascorbic acid in combination with a ROCK inhibitor upon culturing a mesenchymal stem cell and that a type or concentration of ascorbic acid to be used is also important. The present invention has been completed on the basis of these findings. Specifically, the present invention is as described below.

(1) A method for producing a cell sheet comprising a step of culturing mesenchymal stem cells in a medium containing an ascorbic acid species at 0.3 mM or higher and a ROCK (Rho-associated coiled-coil forming kinase) inhibitor to form a sheet-like construct from mesenchymal stem cells in a culture vessel, wherein the medium contains at least a water-soluble ascorbic acid derivative as an ascorbic acid species.

(1-2) The method for producing according to (1), wherein said medium further comprises an ascorbic acid species other than the water-soluble ascorbic acid derivative.

(2) The method for producing according to (1) or (1-2), wherein a period of said culture is 1 to 14 days.

(3) The method for producing according to any of (1) to (2), wherein said mesenchymal stem cell is derived from amnion tissue, fat tissue, or myeloid tissue.

(4) The method for producing according to any of (1) to (3), wherein said water-soluble ascorbic acid derivative is externally added.

(5) The method for producing according to any of (1) to (4), wherein said culture vessel is coated with a temperature-sensitive polymer.

(6) The method for producing according to any of (1) to (5), comprising, a step of peeling said cell sheet from said culture vessel by a physical means, after said culture.

(7) The method for producing according to (6), further comprising a step of stacking comprising incubating said peeled cell sheet stacked on another cell sheet.

(8) The method for producing according to any of (1) to (7), wherein said medium further contains a blood-derived component.

(9) A medium for forming a sheet of mesenchymal stem cells containing an ascorbic acid species, including a water-soluble ascorbic acid derivative, and a ROCK inhibitor, wherein the concentration of said ascorbic acid species is 0.3 mM or higher.

(10) The medium according to (9), which further comprises a blood-derived component.

(11) A kit for forming a sheet of mesenchymal stem cells comprising an ascorbic acid species, including a water-soluble ascorbic acid derivative, a ROCK inhibitor, and a medium.

(12) The kit according to (11), which further comprises a blood-derived component.

(13) The kit according to (11) or (12), for use in adding said ascorbic acid species to a medium at a concentration of 0.3 mM or higher.

(13) An agent for promoting formation of a sheet of mesenchymal stem cells comprising an ascorbic acid species, including a water-soluble ascorbic acid derivative, and a ROCK inhibitor.

(14) The agent for promoting formation of a sheet of mesenchymal stem cells according to (13), further comprising a blood-derived component.

(15) The agent for promoting formation of a sheet of mesenchymal stem cells according to (13) or (14), for use in adding said ascorbic acid species to a medium at 0.3 mM or higher.

Advantageous Effects of Invention

According to the present invention, a high-quality cell sheet of mesenchymal stem cells can be obtained with high efficiency within a short period. In addition, the method for producing according to the present invention is not strictly limited in terms of a culture medium component or a culture vessel to be used, and the method is applicable in a wide range of application.

DESCRIPTION OF EMBODIMENTS

Figure 1:
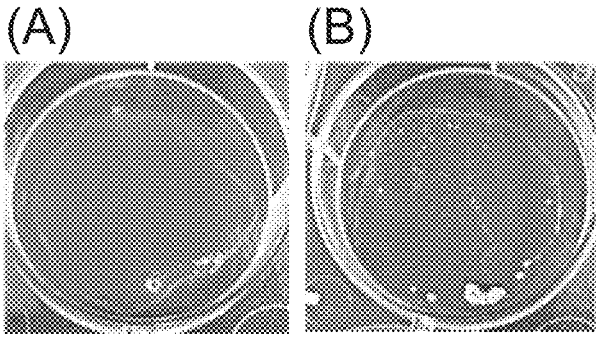
FIG. 1 shows photographs of the cell sheets obtained in Example 1. (A): Example 1-1 (ascorbic acid concentration: 1.87 mM): (B): Example 1-2 (ascorbic acid concentration: 17.2 mM).

Embodiments of the present invention will be specifically described below. The descriptions are intended to facilitate understanding of the principles of the present invention, and therefore, the scope of the present invention is not limited to the embodiments. Other embodiments, to which a person skilled in the art may make modification(s), are also included in the scope of the invention.

The method for producing according to the present invention comprises culturing mesenchymal stem cells in a medium containing an ascorbic acid species at 0.3 mM or higher and a ROCK (Rho-associated coiled-coil forming kinase) inhibitor to form a sheet-like construct from mesenchymal stem cells. The term "mesenchymal stem cells (MSCs)" used herein refers to stem cells that satisfy the definition described below, and are used interchangeably with "mesenchymal stromal cells". The term "mesenchymal stem cells" is also referred to as "MSCs".

Definition of Mesenchymal Stem Cells

Stem Cells that Satisfy the Following Two Requirements:

1) Adherence to plastic in standard medium under culture conditions (a standard medium is prepared by supplementing a basal medium (e.g., αMEM medium) with serum, a serum replacement reagent, or a growth factor (e.g., human platelet lysate as a serum replacement reagent); and 2) Positive for surface antigens CD105, CD73, and CD90 and negative for surface antigen CD45.

The tissue from which the mesenchymal stem cells applied to the method for producing according to the present invention are derived is not particularly limited, and examples thereof include fat, placenta, fetal membrane, amnion, bone marrow, and dental pulp. In particular, mesenchymal stem cells derived from amnion tissue, fat tissue, and bone marrow tissue are preferable, and mesenchymal stem cells derived from amnion tissue are more preferable.

A method for sampling tissue from which the mesenchymal stem cells are derived is not particularly limited. In the case of fat tissue, for example, an arbitrary site (e.g., the abdominal region, the lumbar region, or the femoral region) of a patient is incised by about 0.5 cm to 1 cm with a sharp-pointed surgical knife, and fat is isolated and resected using an arbitrary surgical apparatus (e.g., mosquito forceps or dressing forceps). An incisional wound is single-sutured or fixed with a tape. Fat tissue sampled in such a manner is generally referred to as "resected fat." Alternatively, fat can be suctioned from an arbitrary site (e.g., the abdominal region, the lumbar region, or the femoral region) of a patient using, for example, a cannula. Fat tissue sampled in such a manner is generally referred to as "suctioned fat."

In the case of amnion tissue, fetal appendages, such as the placenta and the fetal membrane, can be sampled at the time of childbirth, and then the amnion can be peeled from the stump end of the fetal membrane. In the case of muscle tissue, muscle tissue can be sampled from the femoral region.

In the case of bone marrow tissue, bone marrow fluid can be sampled by suction after a bone marrow puncture needle is inserted into an arbitrary site (e.g., lumbar bone, thigh bone, shank bone, or iliac bone) of a patient.

A method for separating mesenchymal stem cells from the sampled tissue is not particularly limited, and a common method can be employed. For example, utilizing the fact that mesenchymal stem cells are adhesive cells, mesenchymal stem cells may be seeded as they are in a culture vessel, floating cells may be separated from adhesive cells, and may be thus sampled. Alternatively, in order to separate and sample mesenchymal stem cells, a technique, such as use of a cell separating agent, enzyme treatment, flow cytometry, or density-gradient centrifugation, may also be employed. The sampled mesenchymal stem cells may be washed with a liquid, such as physiological saline. PBS, HBSS(−), or a medium, to further improve the purity of the mesenchymal stem cells.

The mesenchymal stem cells thus sampled as they are may be prepared in the form of a cell sheet by the method for producing according to the present invention without any processing. Alternatively, the mesenchymal stem cells may be first subjected to expansion culture or passage and then to the method for production according to the present invention, if necessary.

A method of expansion culture is not particularly limited, and a common technique can be employed. For example, expansion culture can be performed in the manner described below. First, a cell suspension comprising the sampled mesenchymal stem cells is centrifuged, the supernatant is removed, and the resulting cell pellet is suspended in a medium. Subsequently, the resultant is seeded in an arbitrary culture vessel (e.g., T-25 flask, T-75 flask, or CellSTACK), and culture is performed in an environment with 3% to 5% $CO_2$ concentration and 37° C. in a medium to reach a confluency of 95% or less.

As a medium that can be used herein, a common medium that can be used for mesenchymal stem cell culture can be used. In particular, using a medium containing a blood-derived component, such as a platelet lysate and/or a serum derived from a platelet rich plasma is preferable. Medium exchange may be performed at intervals of arbitrary number of days (e.g., 3 or 4 days) to reach 95% confluence. A period of said culture can be, for example, 2 to 21 days, 3 to 19 days, or 4 to 17 days.

A method for passage of the mesenchymal stem cells thus cultured is not particularly limited, and a common technique can be employed. The passage number is not particularly limited, in terms of mass-production of cells, passage is preferably performed, for example, at least once or at least twice. In addition, the passage number is preferably, for example, 10 or less, 5 or less, or 4 or less, in terms of suppressing cellular aging.

Mesenchymal stem cells subjected to the method for producing according to the present invention may also be cryopreserved before and after the culture or passage, or before (for example, right before) they are subjected to the method for producing. A method of cryopreservation is not particularly limited, and a common technique, such as using a program freezer, a deep freezer or liquid nitrogen, can be employed.

Mesenchymal stem cells subjected to the method for producing according to the present invention are preferably prepared by the method described above. Alternatively, a cell population comprising cells other than mesenchymal stem cells may also be used. In such a case, the cell population preferably satisfies the followings: each proportion of mesenchymal stem cells positive for CD73, CD90, and CD105 is 80% or more and/or each proportion of mesenchymal stem cells negative for CD45 and CD31 is 80% or more, over the cell population. Alternatively, it is preferred that each proportion of mesenchymal stem cells positive for CD73, CD90, and CD105 is 85% or more and/or each proportion of mesenchymal stem cells negative for CD45 and CD31 is 85% or more therein: or that each proportion of mesenchymal stem cells positive for CD73, CD90, and CD105 is 90% or more and/or each proportion of mesenchymal stem cells negative for CD45 and CD31 is 90% or more therein.

CD73 indicates the cluster of differentiation 73 and is a protein also known as 5-nucleotidase or ecto-5'-nucleotidase. CD90 indicates the cluster of differentiation 90 and is a protein also known as Thy-1. CD105 indicates the cluster of differentiation 105 and is a protein also known as Endoglin. CD45 indicates the cluster of differentiation 45 and is a protein also known as PTPRC (protein tyrosine phosphatase, receptor type, C) or LCA (leukocyte common antigen). CD31 indicates the cluster of differentiation 31 and is a protein also known as the Hematopoietic progenitor cell antigen CD31.

In the method for producing according to the present invention, the mesenchymal stem cells are cultured in a medium containing an ascorbic acid species at 0.3 mM or higher and a ROCK inhibitor.

In the present invention, it is necessary to use at least a water-soluble ascorbic acid derivative as an ascorbic acid species.

The term "ascorbic acid species" used herein is an inclusive term indicating a compound including ascorbic acid and an ascorbic acid derivative.

The term "ascorbic acid" refers to a compound represented as (R)-3,4-dihydroxy-5-((S)-1,2-dihydroxyethyl) furan-2(5H)-one. An enantiomer or salt thereof is within the scope of the ascorbic acid herein.

The term "ascorbic acid derivative" used herein refers to a compound or a salt thereof derived from ascorbic acid by substitution of one or more functional groups with other functional groups. The ascorbic acid derivative includes a water-soluble ascorbic acid derivative and a fat-soluble ascorbic acid derivative. The term "water-soluble ascorbic acid derivative" used herein refers to an ascorbic acid derivative that is soluble in water, and the term "fat-soluble ascorbic acid derivative" refers to any ascorbic acid derivative other than the water-soluble ascorbic acid derivative. An amphipathic ascorbic acid derivative is also encompassed in the water-soluble ascorbic acid derivative herein.

The term "water-soluble" refers to properties such that solubility of a substance in water is 10,000 mg/L or higher at 20° C. and an atmospheric pressure of 1. The term "fat-soluble" refers to properties such that solubility of a substance in water is lower than 10,000 mg/L at 20° C. and an atmospheric pressure of 1. A specific solubility of the water-soluble ascorbic acid derivative used in the present invention is not particularly limited, and is, for example, 15,000 mg/L or higher, 20,000 mg/L or higher, 25,000 mg/L or higher, 30,000 mg/L or higher, 50,000 mg/L or higher, 100,000 mg/L or higher, or 130,000 mg/L or higher.

In general, a functional group to be substituted in a water-soluble ascorbic acid derivative is a hydroxy group of ascorbic acid, and the position thereof is not particularly limited. For example, any of a hydroxy group at position 2, a hydroxy group at position 3, a hydroxy group at position 5, a hydroxy group at position 6, or a combination of any thereof may be substituted. Such functional groups can be substituted with, for example, a phosphate group, sugar, alcohol, or a lower alkyl group. Examples of water-soluble ascorbic acid derivatives that can be used in the present invention include, but are not particularly limited to: ascorbic acid ester, such as phosphoric acid ester (e.g., ascorbic acid-2-phosphoric ester, ascorbic acid-3-phosphoric ester, ascorbic acid-6-phosphoric ester, and ascorbic acid-2-polyphosphate ester) and ascorbic acid sulfate ester (e.g., ascorbic acid-2-sulfate ester), ascorbic acid alkyl ether including glyceryl ascorbate (e.g., hexyl 3-glyceryl ascorbate) and other ascorbic acid alkyl ether (e.g., 3-O-ethyl ascorbate); and an ascorbic acid glycoside, such as ascorbic acid-2-glucoside and 2-O-a-D-glucopyranosyl-L-ascorbic acid. In addition, a water-soluble ascorbic acid derivative used in the present invention may also be a compound resulting from further substitution of functional groups in such derivative. For example, such water-soluble ascorbic acid derivative encompasses an amphipathic ascorbic acid derivative, such as ascorbic acid-2-phosphate-6-palmitate or glyceryl octyl ascorbic acid. Further, an ascorbic acid derivative to be used may be any optical isomer. Specifically, any of the L-form, D-form, or racemic form may be used.

Ascorbic acid and an ascorbic acid derivative herein encompass a salt thereof. A type of salt is not particularly limited, and examples thereof include sodium salt, potassium salt, magnesium salt, calcium salt, barium salt, ammonium salt, monoethanolamine salt, diethanolamine salt, triethanolamine salt, monoisopropanolamine salt, and triisopropanolamine salt. Examples of preferable water-soluble ascorbic acid derivatives in the present invention include phosphoric acid ester of ascorbic acid or a salt thereof, ascorbic acid-2-phosphoric acid ester or a salt thereof, and L-ascorbic acid-2-phosphoric acid ester or a salt thereof.

Ascorbic acid species used in the present invention may also be a mixture of a plurality of types of compounds. For example, a plurality of types of derivatives and/or a plurality of types of salts can be used as water-soluble ascorbic acid derivatives. Alternatively, for example, a mixture of ascorbic acid and a water-soluble ascorbic acid derivative can be used as an ascorbic acid species. When a mixture of a plurality of types of compounds is used, the proportion of each compound in the mixture is not particularly limited.

In the present invention, it is important to use the "water-soluble ascorbic acid derivative" as an ascorbic acid species, as described above. Using only ascorbic acid or a salt thereof by itself, which is not an ascorbic acid derivative, or a fat-soluble ascorbic acid derivative (e.g., fatty acid ester, such as ascorbic acid palmitate or L-ascorbic acid stearate), it is impossible to produce a cell sheet of good quality. For example, using some commercially available media by itself, which contains solely a ascorbic acid in a certain amount, it is impossible to produce a cell sheet.

However, it is possible to use a water-soluble ascorbic acid derivative in combination with ascorbic acid, which is not a derivative, and/or a fat-soluble ascorbic acid derivative in the present invention. When it is simply referred to as "ascorbic acid species" hereinbelow, the term refers not only to a water-soluble ascorbic acid derivative, but also to both compounds when the water-soluble ascorbic acid derivative is used in combination with ascorbic acid, which is not a derivative, or the like.

In the method for producing according to the present invention, the concentration of an ascorbic acid species in a medium is not particularly limited, if it is 0.3 mM or higher. For example, such concentration can be 0.31 mM or higher, 0.32 mM or higher, 0.33 mM or higher, 0.34 mM or higher, 0.35 mM or higher, 0.4 mM or higher, 0.5 mM or higher, 0.8 mM or higher, 1.0 mM or higher, or 1.3 mM or higher. The upper limit is not particularly limited, but the concentration of an ascorbic acid species is preferably 40 mM or lower, 35 mM or lower, 30 mM or lower, 20 mM or lower, 10 mM or lower, 8 mM or lower, 6 mM or lower, 5 mM or lower, or 4 mM or lower, in terms of cytotoxicity.

In the method for producing according to the present invention, a method for adjusting the concentration of an ascorbic acid species in a medium within the aforementioned range is not particularly limited. A commercially available medium or additive component to a medium containing a water-soluble ascorbic acid derivative may be used, but it is preferable to externally add a separate water-soluble ascorbic acid derivative to a common medium to adjust the concentration of an ascorbic acid species to a desired level. Alternatively, a compound that is dissolved in water and converted into a water-soluble ascorbic acid derivative may also be added. When a medium or additive component comprises a certain amount of an ascorbic acid species, the concentration thereof may be taken into consideration, so as to adjust the final concentration of an ascorbic acid species in the medium within the aforementioned range. For example, the amount of the water-soluble ascorbic acid derivative to be externally added may be, in the concentration in the medium, 0.1 mM or higher, 0.15 mM or higher, 0.2 mM or higher, 0.3 mM or higher, 0.35 mM or higher, 0.4 mM or higher, 0.5 mM or higher, 0.8 mM or higher, or 1.0 mM or higher. The upper limit is not particularly limited and may be determined in accordance with a preferable total concentration of an ascorbic acid species. For example, the upper limit may be 40 mM or less, 35 mM or less, 30 mM or less, or 20 mM or less.

In the method for producing according to the present invention, a ROCK inhibitor is used. A ROCK inhibitor used in the method for producing according to the present invention is not particularly limited, if it inhibits signal transduction of ROCK (Rho-associated coiled-coil forming kinase) and has activity of contracting a cell, and includes a myosin II inhibitor downstream of the ROCK signal. Specific examples include Y-27632, blebbistatin, ripasudil, fasudil hydrochloride, Y-39983, Wf-536, AZD-5363, GSK-429286A, and thiazovivin.

The concentration of a ROCK inhibitor in a medium is not particularly limited, and a preferable concentration varies depending on a type of a ROCK inhibitor used. For example, the concentration may be 1 μM or higher, 2 μM or higher, 3 μM or higher, 4 μM or higher, 5 μM or higher, 10 μM or higher, 20 μM or higher, or 30 μM or higher. The upper limit is not particularly limited, and the concentration may be, for example, 1,000 μM or lower, 500 μM or lower, 400 μM or lower, 300 μM or lower, 200 μM or lower, 150 μM or lower, or 100 μM or lower. When Y-27632 or ripasudil is used as a ROCK inhibitor, specifically, a preferable concentration is in the range of 1 μM to 500 μM, 3 μM to 400 μM, 5 μM to 350 μM, 10 μM to 300 μM, 20 μM to 200 μM, or 50 μM to 150 μM. When blebbistatin is used, a preferable concentration is in the range of 10 μM to 100 μM or 30 μM to 80 μM. When fasudil hydrochloride is used, a preferable concentration is in the range of 1 μM to 50 μM, 5 μM to 40 μM, 10 μM to 35 M, or 15 μM to 30 μM.

A medium used in the method for producing according to the present invention is not particularly limited for the other components, if the medium contains an ascorbic acid species, including a water-soluble ascorbic acid derivative, and a ROCK inhibitor, and the concentration of an ascorbic acid species is 0.3 mM or higher. For example, the medium may contain other ascorbic acid species or other common culture additives. A medium used to form the cell sheet of the present invention is prepared by, for example, adequately adding an ascorbic acid species, a ROCK inhibitor, and, if necessary, other medium components to a common basal medium used for mesenchymal stem cell culture.

Examples of media that can be used as the basal medium include, but are not particularly limited to, BME medium, BGJb medium, CMRL1066 medium, Glasgow MEM medium, Improved MEM Zinc Option medium, IMDM medium (Iscove's Modified Dulbecco's Medium), Medium 199 medium, Eagle MEM medium, αMEM (Alpha Modification of Minimum Essential Medium Eagle) medium. MEM-α (Minimum Essential Medium a) medium, DMEM medium (Dulbecco's Modified Eagle's Medium), Ham's F10 medium, Ham's F12 medium. RPMI 1640 medium. Fischer's medium, and a mixed medium thereof (e.g., DMEM/F12 medium (Dulbecco's Modified Eagle's Medium/Nutrient Mixture F-12 Ham)). Alternatively, various commercially available serum-free media may be used.

Examples thereof include, but are not particularly limited to, STK1 and STK2 (DS Pharma Biomedical Co., Ltd.), EXPREP MSC Medium (BioMimetics Sympathies Inc.), and Corning stemgro human mesenchymal stem cell medium (Corning Inc.).

Examples of other components to be added to said basal medium include, such as albumin, a blood-derived component, and a growth factor. In an aspect in which albumin is added to said basal medium, the albumin concentration is preferably 0.05% by mass or higher and 5% by mass or lower. Examples of blood-derived components include various sera (e.g., animal-derived serum such as fetal bovine serum (FBS or FCS), human serum, and serum prepared from a platelet rich plasma or platelet lysate derived from the blood of various animals and/or a human, platelet lysates derived from the blood of various animals and/or a human (hPL), and plasma. Human serum may be derived from either an individual who is identical to the individual from which tissue comprising adhesive cells was obtained or another individual. In an aspect in which a blood-derived component is added to said basal medium, the concentration of the blood-derived component is, for example, 2% by volume or higher and 40% by volume or lower, 3% by volume or higher and 30% by volume or lower, 4% by volume or higher and 20% by volume or lower, or 5% by volume or higher and 15% by volume or lower. In the method for producing according to the present invention, it is preferable to add, as a blood-derived component, a human-derived platelet lysate to a medium in the step of forming a sheet, or to use mesenchymal stem cells cultured under the condition of using a medium supplemented with a human-derived platelet lysate in the step of culture before the step of forming a sheet.

In an aspect in which a growth factor is added, a reagent for stabilizing a growth factor in a medium (e.g., an anticoagulant such as heparin, a gel, or a polysaccharide) may be added in addition to a growth factor, or a growth factor stabilized in advance may be added to said basal medium. Examples of growth factors that may be used include, but are not particularly limited to, fibroblast growth factor (FGF), epithelial cell growth factor (EGF), transforming growth factor (TGF), vascular endothelial cell growth factor (VEGF), platelet-derived growth factor (PDGF), and their families.

In the method for producing according to the present invention, a cell sheet is produced by culturing mesenchymal stem cells in the medium to form a sheet-like construct. In the method for producing according to the present invention, a method of culture is not particularly limited. For example, floating culture, adhesion culture, or the combination thereof may be employed. In the method for producing according to the present invention, a preferable method of culture is adhesion culture. According to the method for producing according to the present invention, a cell sheet of good quality may be produced even using a common culture vessel made in plastic that can be used for mesenchymal stem cell culture because the afore-mentioned particular medium is used.

In order to produce a cell sheet with better quality or improve ease of handling, a culture vessel coated with a temperature-sensitive polymer may be used. The term "temperature-sensitive polymer (also referred to as a "temperature-responsive polymer") refers to a polymer that reversibly changes between hydrophobicity (cell adhesive property) and hydrophilicity (cell detaching property) at a particular temperature as a threshold. Using a culture vessel coated with such polymer, cells can be detached from the culture vessel only by changing temperature while maintaining the form of the cells. For example, a culture vessel coated with poly-N-propylacrylamide (PIPAAm) that exhibits a change between hydrophobicity and hydrophilicity in water at 32° C. (tradename: UpCell) as a threshold may be used, and a culture vessel equivalent thereto can also be used.

In the present invention, a culture vessel may be coated with an extracellular matrix (ECM) protein in advance, to further promote cell adhesion or proliferation. Examples of extracellular matrices include, but are not particularly limited to, collagen, elastin, fibronectin, and laminin. A known method may be employed as a coating method.

A form of a culture vessel is not particularly limited, and a culture vessel in a well form or a dish form may preferably be used. In terms of cell sheet formation and maintenance of the form thereof, a culture vessel having a flat bottom is preferable. In the case of a flat-bottom vessel, a form of the bottom is not particularly limited. For example, a culture vessel having a round or square bottom may be used. When the method of the present invention is performed using a flat-bottom vessel, in general, a cell sheet having a form similar to the form of the bottom of the culture vessel is formed. Thus, a culture vessel may be selected in accordance with a form of interest.

In the method for producing according to the present invention, a cell suspension of mesenchymal stem cells or the like is seeded in the culture vessel, and cells are cultured to confluency of 95% or less in under the environment of $CO_2$ concentration of 3% or higher and 5% or lower and 37° C. using the medium to form a cell sheet. Culture conditions are not limited thereto, if the conditions are suitable for a method for culturing mesenchymal stem cells.

The seeding density is not particularly limited. For example, the seeding density may be 500 to 500.000 cells/$cm^2$. The seeding density is more preferably 1,000 cells/$cm^2$ or more, 2,000 cells/$cm^2$ or more, or 5,000 cells/$cm^2$ or more. In order to prepare a cell sheet of particularly good quality, a seeding density that is higher than the seeding density generally employed for expansion culture of mesenchymal stem cells is preferable, and it is 10,000 cells/$cm^2$ or more, or 50,000 cells/$cm^2$ or more. The upper limit is not particularly limited, but it is preferably 200,000 cells/$cm^2$ or less, 150,000 cells/$cm^2$ or less, or 120,000 cells/$cm^2$ or less.

The number of days of culture is not particularly limited, and it is, for example, 1 day or longer, 2 days or longer, 3 days or longer, 4 days or longer, or 5 days or longer. While the upper limit is also not particularly limited, a sheet can be prepared within a relatively short period time by the method for producing according to the present invention. A cell sheet can be obtained within 14 days or within 10 days, within 7 days, or within 6 days depending on the conditions.

A form of a cell sheet formed by the method for producing according to the present invention is not particularly limited. As describe above, a form of a cell sheet can vary depending on, for example, a type of a culture vessel used or a form of the bottom of the culture vessel. Alternatively, an auxiliary frame to adjust a form may be used. Specifically, for example, a cell sheet in an approximately round form, oval form, or square form can be obtained.

It is preferable that the cell sheet obtained by the method of the present invention be able to maintain a planar form at the time of peeling or handling after peeling (e.g., at the time of storage while floating in a liquid). Referring to the situation in which a planar form is maintained, a state in which an irreversible or complicated fold line is not formed and a form is not significantly changed is maintained.

The cell sheet formed by the method of the present invention is preferably uniform in thickness. Referring to the situation in which a cell sheet is uniform in thickness, across a 90% or larger area of the cell sheet, the thickness thereof is substantially the same. Whether a cell sheet is uniform in thickness may be determined by actually measuring thickness or visual inspection. Thickness may be measured by, for example, cutting a cell sheet and observing the cross section thereof under a microscope. In addition, for example, when unevenness is not observed in the color of the cell sheet plane (white, in general) by visually inspecting the plane thereof in a floating state, the cell sheet can be determined to be uniform in thickness. Thickness of a cell sheet is not particularly limited. For example, thickness of a sheet may be 2 μm or thicker, 5 μm or thicker, 8 μm or thicker, or 10 μm or thicker.

A size of a cell sheet is not particularly limited. In general, a size of a cell sheet can vary depending on the number of days of culture, the bottom area of the culture vessel, and other conditions. For example, an area of a cell sheet is 40% or larger, 45% or larger, 50% or larger, 55% or larger, 60% or larger, 65% or larger, 70% or larger, or 75% or larger of the bottom area of the culture vessel 7 days after the initiation of culture. An area of a cell sheet, for example, in their longer diameter, is 20 mM or longer, 25 mM or longer, 26 mM or longer, 27 mM or longer, 28 mM or longer, 29 mM or longer, 30 mM or longer, 31 mM or longer, 32 mM or longer, or 35 mM or longer. The term “longer diameter” used herein refers to a length in the longitudinal direction of the cell sheet; i.e., a diameter of the minimum circumcircle of the cell sheet.

The method for producing according to the present invention may further comprise a step of peeling a cell sheet after the cell sheet is formed via the culture as described above. The cell sheet obtained by the method for producing according to the present invention has sufficient strength, and can be sufficiently peeled only by a physical means, such as the use of forceps or via pipetting. In order to improve ease of handling, a support (e.g., tradename: CellShifter) developed for collecting cell sheet may be used by itself or in combination.

In the present invention, in addition, cell sheets may be stacked. Cell sheets can be stacked by, for example, stacking a plurality of cell sheets obtained by the method of producing on each other and incubating the resultant for approximately 2 to 30 minutes. The number of cell sheets to be stacked is not particularly limited. For example, 2, 3, 4, or 5 cell sheets may be stacked. When 3 or more cell sheets are to be stacked, 3 sheets may be stacked at a time, a cell sheet may be stacked on another sheet, or a stack of cell sheets may be stacked on another stack of cell sheets.

Types of cells constituting cell sheets to be stacked or culture conditions for each cell sheet culture can be independently selected. For example, cell sheets prepared from the same type of cells under the same culture conditions may be stacked on each other, or cell sheets prepared from different types of cells under different culture conditions may be stacked on each other.

Upon stacking, an arbitrary substance can be added between cell sheets. Examples of substances that can be added include a substance that promotes adhesion between cell sheets (e.g., a scaffold and a matrix), a substance that promotes intercellular communication between cell sheets (e.g., an elongation inducer and a migration inducer), fibronectin, a growth promoter, a nutritional factor, a differentiation promoter or inhibitor, and a combination thereof. A method of addition is not particularly limited. For example, such arbitrary substance can be added by directly coating, spraying, or adding dropwise to the surface of a cell sheet or soaking the cell sheets in a medium supplemented with the substance.

In order to facilitate peeling or stacking of the cell sheets obtained, the support as described above or the like can be adequately used. By stacking cell sheets, the cell sheets become more durable, handling thereof becomes easy, and the cell count per unit area is increased. By stacking cell sheets, in addition, cell sheet thickness may be 15 μm or more, 20 μm or more, or 30 μm or more.

The present invention also relates to a cell sheet produced by the method of the present invention.

The cell sheet of mesenchymal stem cells obtained by the method for producing according to the present invention can be used in a wide variety of fields including medical application.

In addition, the present invention relates to a medium for forming a sheet of mesenchymal stem cells comprising an ascorbic acid species, including a water-soluble ascorbic acid derivative, and a ROCK inhibitor in which the concentration of an ascorbic acid species is 0.3 mM or higher.

For the medium for forming a sheet of mesenchymal stem cells, an ascorbic acid species, a water-soluble ascorbic acid derivative, a ROCK inhibitor, and a medium similar to those that can be used in the method for producing a cell sheet may be used. This medium can optionally contain other components, such as a blood-derived component and an additional ascorbic acid species. The medium may be provided at a high concentration to be used in the present invention after dilution.

At least a part of an ascorbic acid species, including a water-soluble ascorbic acid derivative, a ROCK inhibitor, and a medium may be provided in separate vessels. In such a case, it can be prepared in the form of a kit for producing a sheet of mesenchymal stem cells comprising an ascorbic acid species, including a water-soluble ascorbic acid derivative, a ROCK inhibitor, and a medium.

In using the kit of the present invention, an ascorbic acid species, including a water-soluble ascorbic acid derivative, are added to a medium to adjust the concentration of an ascorbic acid species to 0.3 mM or higher. For example, a kit may be prepared as a kit comprising a medium supplemented with an ascorbic acid species, including a water-soluble ascorbic acid derivative, at a concentration of 0.3 mM or higher, and a ROCK inhibitor. Information concerning the amount of the water-soluble ascorbic acid derivative and/or an ascorbic acid species to be added may also be provided by means of the instruction manual, or the like.

Using the water-soluble ascorbic acid derivative, the ascorbic acid species, and the ROCK inhibitor at the concentration described above, formation of a cell sheet of mesenchymal stem cells can be promoted.

Accordingly, the present invention further relates to an agent for promoting formation of a sheet of mesenchymal stem cells comprising an ascorbic acid species, including a water-soluble ascorbic acid derivative, and a ROCK inhibitor, and use of an ascorbic acid species, including a water-soluble ascorbic acid derivative, and a ROCK inhibitor in production of a sheet of mesenchymal stem cells.

Concerning the agent for promoting formation of a sheet of mesenchymal stem cells and the use, an ascorbic acid species, a water-soluble ascorbic acid derivative, and a ROCK inhibitor similar to those that can be used in the method for producing a cell sheet may be used. This agent can optionally comprise other components, such as a blood-derived component and an additional ascorbic acid species.

This agent is an agent for promoting formation of a cell sheet used to add an ascorbic acid species, including a water-soluble ascorbic acid derivative, to a medium at 0.3 mM or higher. This agent may be provided in the portioned forms for use in a particular volume of a medium, and information concerning the amount of the water-soluble ascorbic acid derivative and/or the ascorbic acid species to be added may also be provided by means of the instruction manual, or the like.

EXAMPLES

The present invention will be described in greater detail with reference to the Examples below; however, the Examples demonstrate specific examples of the present invention and the present invention is not limited to the Examples.

Example 1 and Comparative Example 1

MEMα medium (Thermo Fisher Scientific) was supplemented with hPL (AventaCell BioMedical Corp.) at 5% by volume and Y-27632 (FUJIFILM Wako Pure Chemical Corporation) at 100 μM, and an L-ascorbic acid phosphate magnesium salt hydrate (FUJIFILM Wako Pure Chemical Corporation) was adequately added thereto to prepare media each having a concentration of an ascorbic acid species as shown in Table 1. Using the media thus prepared, culture conditions for forming a cell sheet from amnion-derived mesenchymal stem cells were examined. The amnion-derived mesenchymal stem cells were seeded at $1\times10^5$ cells/cm$^2$ in a temperature-responsive culture dish (tradename: UpCell: CellSeed) coated with fibronectin (Sigma-Aldric) in advance and cultured in the medium under the conditions of 37° C. and 5% $CO_2$ for 7 days. After the completion of culture, a support (tradename: CellShifter: CellSeed) for collecting cell sheet was stacked on the cell sheet formed in the culture vessel, and the cell sheet was peeled from the culture dish together with the support using forceps. The cell sheet was peeled from the support, and whether the cell sheet was formed and the form thereof were evaluated.

In Comparative Example 1 in which the concentration of an ascorbic acid species in the medium was 0.17 mM, cells did not form a sheet. In contrast, in Examples 1-1 and 1-2 in which the concentration of an ascorbic acid species in the medium was 0.3 mM or higher, a cell sheet in a good form was obtained. FIG. 1 shows the form of the cell sheet obtained.

TABLE 1

| | Concentration of ascorbic acid species in medium (mM) | Sheet formation |
|---|---|---|
| Comp. Ex. 1 | 0.17 | Poor |
| Ex. 1-1 | 1.87 | Good |
| Ex. 1-2 | 17.2 | Good |

Good: Sheet was formed, good in form
Poor: Sheet was not formed

Example 2 and Comparative Example 2

To MEMα medium supplemented with hPL at 5% by volume or FBS (Moregate) at 10% by volume, as a blood-derived component, Y-27632 and an L-ascorbic acid phosphate magnesium salt hydrate were adequately added to prepare media each having a concentration of Y-27632 and an ascorbic acid species as shown in Table 2. With the use of the media thus prepared, culture conditions for forming a cell sheet from amnion-derived mesenchymal stem cells were examined. In the same manner as in Example 1, the amnion-derived mesenchymal stem cells were seeded at $1\times10^5$ cells/cm$^2$ in a fibronectin-coated temperature-responsive culture dish and cultured under the conditions of 37° C. and 5% $CO_2$ for 4 days. After the completion of culture, the cell sheet was collected using a support for collecting cell sheet in the same manner as in Example 1, and whether the cell sheet was formed and the form thereof were evaluated.

Figure 2:
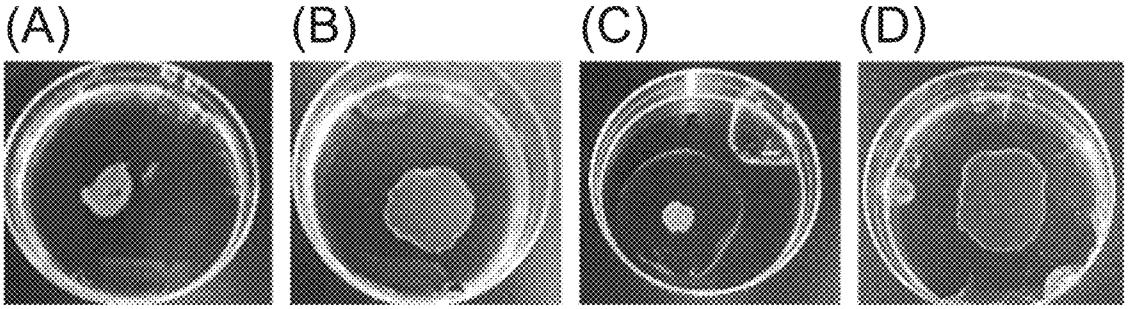
FIG. 2 shows photographs of the cell sheets obtained in Example 2 and in Comparative Example 2. (A): Comparative Example 2-3 (hPL+ascorbic acid (0.17 mM)+Y-27632): (B) Example 2-1 (hPL+ascorbic acid (1.7 mM)+Y-27632): (C): Comparative Example 2-4 (FBS+ascorbic acid (0.17 mM)); (D): Example 2-2 (FBS+ascorbic acid (1.7 mM)+Y-27632).

In Comparative Examples 2-1 and 2-2 in which a medium not supplemented with Y-27632, a ROCK inhibitor, was used, cells did not form a sheet. In Comparative Example 2-3 and Comparative Example 2-4 in which the concentration of ascorbic acid species in the medium was lower than 0.3 mM, cells formed a sheet in the culture vessel. However, the sheet was not very good in its form, and was torn when peeled, and thus, a cell sheet durable in practical use could not be obtained. In contrast, in Example 2-1 and Example 2-2 in which the concentration of an ascorbic acid species in the medium was 0.3 mM or higher, a cell sheet in a good form was obtained, and a cell sheet was easily collected using forceps. FIG. 2 shows the form of the cell sheet obtained.

TABLE 2

| | Serum | Concentration of Y-27632 in medium (μM) | Concentration of ascorbic acid species in medium (mM) | Sheet formation |
|---|---|---|---|---|
| Comp. Ex. 2-1 | hPL | 0 | 0.17 | Poor |
| Comp. Ex. 2-2 | | | 1.7 | Poor |
| Comp. Ex. 2-3 | | 100 | 0.17 | Fair |
| Ex. 2-1 | | | 1.7 | Good |
| Comp. Ex. 2-4 | FBS | 0 | 0.17 | Fair |
| Ex. 2-2 | | 100 | 1.7 | Good |

Good: Sheet was formed, good in form
Fair: Sheet was formed, poor in form
Poor: Sheet was not formed

Example 3 and Comparative Example 3

Figure 3:
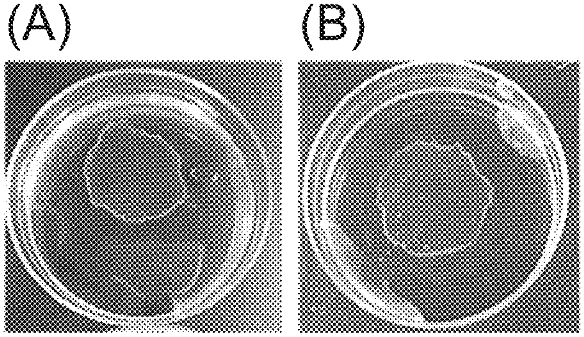
FIG. 3 shows photographs of the cell sheets obtained in Example 5. (A): Example 5-1 (hPL+ascorbic acid+Y-27632)): (B): Example 5-2 (FBS+ascorbic acid+Y-27632).

To MEMα medium supplemented with hPL at 5% by volume as a blood-derived component, Y-27632 and an L-ascorbic acid phosphate magnesium salt hydrate were adequately added to prepare media each having a concentration of Y-27632 and an ascorbic acid species as shown in Table 3. Using the media thus prepared, culture conditions for forming a cell sheet from amnion-derived mesenchymal stem cells were examined. In the same manner as in Example 1, the amnion-derived mesenchymal stem cells were seeded at $1\text{-}10^5$ cells/cm$^2$ in a fibronectin-coated temperature-responsive culture dish and cultured in the medium under the conditions of 37° C. and 5% $CO_2$ for 5 days. After the completion of culture, the cell sheet was peeled via pipetting, and whether the cell sheet was formed was evaluated. FIG. 3 shows the results of formation of the cell sheet obtained.

TABLE 3

| | Concentration of Y-27632 in medium (μM) | Concentration of ascorbic acid species in medium (mM) | Sheet formation |
|---|---|---|---|
| Comp. Ex. 3-1 | 30 | 0.17 | Fair |
| Ex. 3-1 | | 0.34 | Good |
| Ex. 3-2 | | 1.02 | Good |
| Ex. 3-3 | | 3.40 | Good |
| Ex. 3-4 | | 10.2 | Good |
| Comp. Ex. 3-2 | 100 | 0.17 | Fair |
| Ex. 3-5 | | 0.34 | Excellent |
| Ex. 3-6 | | 1.02 | Excellent |
| Ex. 3-7 | | 3.40 | Excellent |
| Ex. 3-8 | | 10.2 | Excellent |
| Ex. 3-9 | | 34.0 | Excellent |

Excellent: Sheet was formed, very good in form and strength
Good: Sheet was formed, good in form
Fair: Sheet was formed, poor in form When the concentration of an ascorbic acid species in the medium was 0.3 mM or higher, a cell sheet in a good form was formed. When the concentration of Y-27632 in the medium was 100 μM, in particular, particularly good formation of a sheet was observed, the cell sheet obtained was in a very good form, and the sheet had strength to the extent that the sheet would not be torn even when it was pulled with forceps somewhat strongly.

Example 4 and Comparative Example 4

Figure 4:
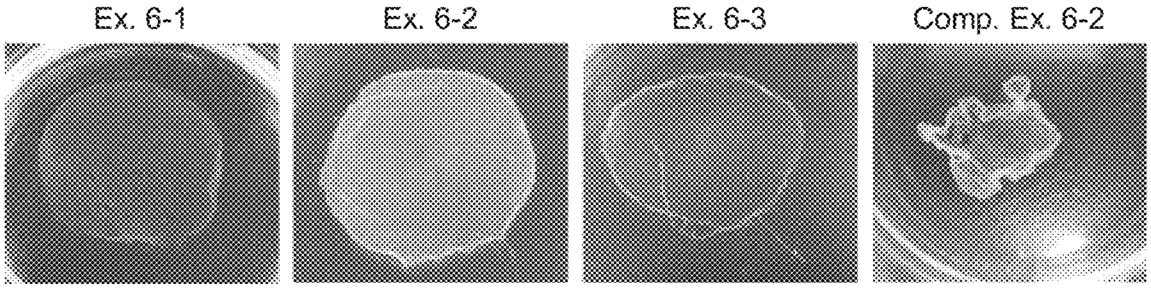
FIG. 4 shows photographs of the cell sheets obtained in Example 6 and in Comparative Example 6.

To MEMα medium supplemented with hPL at 5% by volume as a blood-derived component, a ROCK inhibitor (blebbistatin, ripasudil, or fasudil hydrochloride) and an L-ascorbic acid phosphate magnesium salt hydrate were adequately added to prepare media each having a concentration of the ROCK inhibitor and an ascorbic acid species as shown in Table 4. Using the media thus prepared, culture conditions for forming a cell sheet from amnion-derived mesenchymal stem cells were examined. In the same manner as in Example 1, the amnion-derived mesenchymal stem cells were seeded at $1\times10^5$ cells/$cm^2$ in a fibronectin-coated temperature-responsive culture dish and cultured under the conditions of 37° C. and 5% $CO_2$ for 5 days. After the completion of culture, the cell sheet was peeled via pipetting, and whether the cell sheet was formed was evaluated. FIG. 4 shows the results of formation of the cell sheet obtained.

TABLE 4

| | ROCK inhibitor used | Concentration of ROCK inhibitor in medium (μM) | Concentration of ascorbic acid species in medium (mM) | Sheet formation |
|---|---|---|---|---|
| Comp. Ex. 4-1 | Blebbistatin | 10 | 0.17 | Poor |
| Ex. 4-1 | | | 0.34 | Good |
| Comp. Ex. 4-2 | | 30 | 0.17 | Fair |
| Ex. 4-2 | | | 0.34 | Excellent |
| Ex. 4-3 | | | 1.02 | Excellent |
| Ex. 4-4 | | | 10.2 | Excellent |
| Ex. 4-5 | Ripasudil | 3 | 0.34 | Good |
| Comp. Ex. 4-3 | | 10 | 0.17 | Fair |
| Ex. 4-6 | | | 0.34 | Excellent |
| Ex. 4-7 | | | 3.40 | Good |
| Comp. Ex. 4-4 | | 30 | 0.17 | Fair |
| Ex. 4-8 | | | 0.34 | Excellent |
| Ex. 4-9 | | | 3.40 | Excellent |
| Ex. 4-10 | | | 10.2 | Good |
| Comp. Ex. 4-5 | | 100 | 0.17 | Fair |
| Ex. 4-11 | | | 0.34 | Excellent |
| Ex. 4-12 | | | 3.40 | Excellent |
| Ex. 4-13 | | | 34.0 | Excellent |
| Ex. 4-14 | | 300 | 34.0 | Excellent |
| Comp. Ex. 4-6 | Fasudil hydrochloride | 10 | 0.17 | Poor |
| Ex. 4-15 | | | 0.34 | Good |
| Comp. Ex. 4-7 | | 30 | 0.17 | Fair |
| Ex. 4-16 | | | 0.34 | Excellent |
| Ex. 4-17 | | | 1.02 | Good |

Excellent: Sheet was formed, very good in form and strength
Good: Sheet was formed, good in form
Fair: Sheet was formed, poor in form When using a medium having a concentration of an ascorbic acid species at 0.3 mM or higher and containing the ROCK inhibitor, a cell sheet in a good form was formed. However, a combination of the optimal concentration of an ascorbic acid species and that of the ROCK inhibitor was found to vary depending on the type of the ROCK inhibitor.

Example 5 and Comparative Example 5

To MEMα medium supplemented with hPL at 5% by volume or FBS at 10% by volume, as a blood-derived component, Y-27632 and an L-ascorbic acid phosphate magnesium salt hydrate were adequately added to prepare media each having a concentration of Y-27632 and an ascorbic acid species as shown in Table 5. Using the media thus prepared, culture conditions for forming a cell sheet from amnion-derived mesenchymal stem cells were examined. In Example 5 and Comparative Example 5, the amnion-derived mesenchymal stem cells were seeded at $1\times10^5$ cells/$cm^2$ in a common 6-well plate (tradename: Coster 6-well transparent multi-well plate for cell culture, Corning) and cultured under the conditions of 37° C. and 5% $CO_2$ for 7 days. After the completion of culture, the cell sheet was collected using a support for collecting cell sheet in the same manner as in Example 1, and whether the cell sheet was formed and the form thereof were evaluated. In Comparative Example 5-2 in which the Y-27632-free medium having a concentration of an ascorbic acid species at lower than 0.3 mM was used, cells did not form a sheet. In Comparative Example 5-1, cells formed a sheet but the form thereof was poor, and the obtained sheet was likely to be tom very easily. In contrast, in Example 5-1 and Example 5-2 in which the medium having a concentration of an ascorbic acid species at 0.3 mM or higher and containing Y-27632 was used, a cell sheet was obtained in a good form and was easily peeled without using a temperature-sensitive cell vessel. FIG. 3 shows the form of the obtained cell sheet.

TABLE 5

| | Serum | Concentration of Y-27632 in medium (μM) | Concentration of ascorbic acid species in medium (mM) | Sheet formation |
|---|---|---|---|---|
| Comp. Ex. 5-1 | hPL | 0 | 0.17 | Fair |
| Ex. 5-1 | | 100 | 1.7 | Good |
| Comp. Ex. 5-2 | FBS | 0 | 0.17 | Poor |
| Ex. 5-2 | | 100 | 1.7 | Good |

Good: Sheet was formed, good in form
Fair: Sheet was formed, poor in form
Poor: Sheet was not formed

Example 6 and Comparative Example 6

Figure 6:
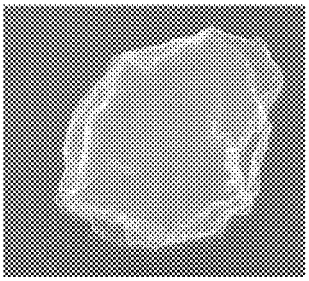
FIG. 6 shows a photograph of the stacked cell sheets obtained in Example 8.

To MEMα medium supplemented with hPL at 5% by volume as a blood-derived component, Y-27632 and an L-ascorbic acid phosphate magnesium salt hydrate were adequately added to prepare media each having a concentration of Y-27632 and an ascorbic acid species as shown in Table 6. Using the media thus prepared, culture conditions for forming a cell sheet from mesenchymal stem cells, which were obtained from the tissue, shown in Table 6 were examined. In the same manner as in Example 1, the mesenchymal stem cells derived from amnion tissue, fat tissue, or bone marrow tissue were seeded at $1\times10^5$ cells/cm$^2$ in a fibronectin-coated temperature-responsive culture dish and cultured in the medium under the conditions of 37° C. and 5% $CO_2$ for 5 days. After the completion of culture, the cell sheet was peeled using a support for collecting cell sheet, and whether the cell sheet was formed was evaluated FIG. 6 shows the results of formation of the cell sheet.

TABLE 6

| | Origin tissue of MSCs | Serum | Concentration of Y-27632 in medium (μM) | Concentration of ascorbic acid species in medium (mM) | Sheet formation |
|---|---|---|---|---|---|
| Comp. Ex. 6-1 | Amnion | hPL | 0 | 0.17 | Poor |
| Ex. 6-1 | | | 100 | 1.7 | Good |
| Comp. Ex. 6-2 | Fat | | 0 | 0.17 | Fair |
| Ex. 6-2 | | | 100 | 1.7 | Good |
| Comp. Ex. 6-3 | Bone marrow | | 0 | 0.17 | Poor |
| Ex. 6-3 | | | 100 | 1.7 | Good |

Good: Sheet was formed, good in form
Fair: Sheet was formed, poor in form
Poor: Sheet was not formed In Example 6-1. Example 6-2, and Example 6-3 in which the medium having a concentration of an ascorbic acid species at 0.3 mM or higher and containing Y-27632 was used, a cell sheet in a good form was formed. It was thus confirmed that a cell sheet could be nicely formed using the method for producing according to the present invention, regardless of the origin of mesenchymal stem cells. In Comparative Example 6-1 and Comparative Example 6-3 in which the Y-27632-free medium having a concentration of an ascorbic acid species at lower than 0.3 mM was used, cells did not form a sheet. In Comparative Example 6-2, cells formed a sheet but the form thereof was poor, and the obtained sheet was likely to be tom. FIG. 4 shows the form of the obtained cell sheet.

Example 7 and Comparative Example 7

To MEMα medium supplemented with hPL at 5% by volume as a blood-derived component, Y-27632 and an ascorbic acid species were added to prepare media each having a concentration of Y-27632 and an ascorbic acid species (L-ascorbic acid phosphate magnesium salt hydrate, 2-O-a-D-glucopyranosyl-L-ascorbic acid, 6-O-palmitoyl-L-ascorbic acid, sodium isoascorbate monohydrate, or sodium L(+)-ascorbate) as shown in Table 7. Using the media thus prepared, culture conditions for forming a cell sheet from amnion-derived mesenchymal stem cells were examined. In the same manner as in Example 1, the amnion-derived mesenchymal stem cells were seeded at $1\times10^5$ cells/cm$^2$ in a fibronectin-coated temperature-responsive culture dish and cultured in the medium under the conditions of 37° C. and 5% $CO_2$ for 5 days. After the completion of culture, the cell sheet was peeled using a support for collecting cell sheet, and whether the cell sheet was formed was evaluated. FIG. 7 shows the results of formation of the cell sheet obtained.

TABLE 7

| | Ascorbic acids used | Concentration of ascorbic acid species in medium (mM) | Concentration of Y-27632 in medium (μM) | Sheet formation |
|---|---|---|---|---|
| Ex. 7-1 | L-Ascorbic acid phosphate magnesium salt hydrate | 1.7 | 100 | Good |
| Ex. 7-2 | 2-O-a-D-Glucopyranosyl-L-ascorbic acid | | | Good |
| Comp. Ex. 7-1 | 6-O-Palmitoyl-L-ascorbic acid | | | Poor |
| Comp. Ex. 7-2 | Sodium isoascorbate monohydrate | | | Poor |
| Comp. Ex. 7-3 | Sodium L(+)-ascorbate | | | Poor |

Good: Sheet was formed, good in form
Poor: Sheet was not formed

Figure 5:
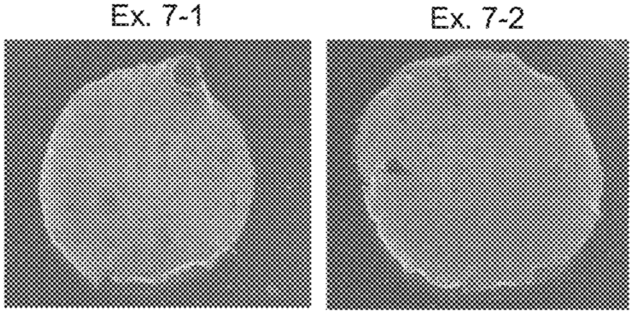
FIG. 5 shows photographs of the cell sheets obtained in Example 7.

In Example 7-1 in which an L-ascorbic acid phosphate magnesium salt hydrate, a water-soluble ascorbic acid derivative, was used and Example 7-2 in which 2-O-a-D-glucopyranosyl-L-ascorbic acid was used, a cell sheet in a good form was obtained. In Comparative Example 7-1 in which 6-O-palmitoyl-L-ascorbic acid, a fat-soluble ascorbic acid derivative, was used, Comparative Example 7-2 in which a D-sodium isoascorbate monohydrate, which is not a derivative, was used, and Comparative Example 7-3 in which sodium L(+)-ascorbate was used, cells did not form a sheet. FIG. 5 shows the form of the obtained cell sheet.

Example 8

In the same manner as in Example 1, the amnion tissue-derived mesenchymal stem cells were seeded at $1\times10^5$ cells/cm$^2$ in a fibronectin-coated temperature-responsive culture dish. To MEMα medium supplemented with hPL at 5% by volume as a blood-derived component, Y-27632 and an L-ascorbic acid phosphate magnesium salt hydrate were adequately added to prepare media each having a concentration of Y-27632 and an ascorbic acid species as shown in Table 8. Using the media thus prepared, culture was performed under the conditions of 37° C. and 5% $CO_2$ for 5 days. After the completion of culture, the cell sheets were peeled from the temperature-responsive culture dish using the support for collecting cell sheet, and the first cell sheet was stacked on the second cell sheet together with the support. The support and the two cell sheets were peeled from the temperature-responsive culture dish, and the two cell sheets were stacked on the third cell sheet together with the support. The support and the three cell sheets were peeled from the temperature-responsive culture dish, and MEMα medium supplemented with 5% by volume of hPL was added dropwise thereto, then incubated at 37° C. for 10 minutes. The cell sheets were peeled from the support, and the stacked cell sheets were thus obtained.

TABLE 8

| | Serum | Concentration of Y-27632 in medium (μM) | Concentration of ascorbic acid species in medium (mM) | Acquisition of stacked sheets |
|---|---|---|---|---|
| Ex. 8 | hPL | 100 | 1.7 | Good |

Good: Stacked sheets were obtained

In the stacked cell sheets, cell sheets were found to be attached to each other to the extent that the cell sheets would not be peeled from each other via pipetting with a micropipette. FIG. 6 shows the form of the stacked sheets obtained.

The invention claimed is:

1. A method for producing a cell sheet comprising a step of:

culturing mesenchymal stem cells in a medium containing an ascorbic acid species at 0.5 mM or higher and a ROCK (Rho-associated coiled-coil forming kinase) inhibitor to form a cell sheet comprising mesenchymal stem cells in a culture vessel, wherein the medium contains at least a water-soluble ascorbic acid derivative as an ascorbic acid species.

2. The method for producing according to claim 1, wherein said medium further comprises an ascorbic acid species other than the water-soluble ascorbic acid derivative.

3. The method for producing according to claim 1, wherein a period of said culture is 1 to 14 days.

4. The method for producing according to claim 1, wherein said mesenchymal stem cells are derived from amnion tissue, fat tissue, or myeloid tissue.

5. The method for producing according to claim 1, wherein said water-soluble ascorbic acid derivative is externally added.

6. The method for producing according to claim 1, wherein said culture vessel is coated with a temperature-sensitive polymer.

7. The method for producing according to claim 1, comprising, a step of peeling said cell sheet comprising mesenchymal stem cells from said culture vessel by a physical means, after said culture.

8. The method for producing according to claim 7, further comprising a step of stacking said cell sheet comprising mesenchymal stem cells on another cell sheet and incubating said peeled cell sheet comprising mesenchymal stem cells while stacked on said another cell sheet.

9. The method for producing according to claim 1, wherein said medium further contains a blood-derived component.

* * * * *